United States Patent
Kitakawa et al.

(10) Patent No.: US 11,014,903 B2
(45) Date of Patent: May 25, 2021

(54) VITAMIN E PRODUCTION METHOD AND VITAMIN E PRODUCTION DEVICE

(71) Applicant: TOHOKU UNIVERSITY, Sendai (JP)

(72) Inventors: Naomi Kitakawa, Sendai (JP); Kousuke Hiromori, Sendai (JP); Sayaka Hosokawa, Sendai (JP); Tomoya Watanabe, Sendai (JP)

(73) Assignee: PHYTOCHEM PRODUCTS INC., Miyagi (JP)

( * ) Notice: Subject to any disclaimer, the term of this patent is extended or adjusted under 35 U.S.C. 154(b) by 0 days.

(21) Appl. No.: 16/485,602

(22) PCT Filed: Feb. 16, 2018

(86) PCT No.: PCT/JP2018/005526
§ 371 (c)(1),
(2) Date: Aug. 13, 2019

(87) PCT Pub. No.: WO2018/151261
PCT Pub. Date: Aug. 23, 2018

(65) Prior Publication Data
US 2020/0002305 A1 Jan. 2, 2020

(30) Foreign Application Priority Data
Feb. 17, 2017 (JP) .............................. JP2017-028299

(51) Int. Cl.
*C07D 311/72* (2006.01)
*B01J 41/05* (2017.01)
*B01D 15/18* (2006.01)
*B01D 15/36* (2006.01)
*B01D 15/42* (2006.01)
*C11C 3/00* (2006.01)

(52) U.S. Cl.
CPC ........ *C07D 311/72* (2013.01); *B01D 15/1871* (2013.01); *B01D 15/363* (2013.01); *B01D 15/424* (2013.01); *B01J 41/05* (2017.01); *C11C 3/003* (2013.01)

(58) Field of Classification Search
CPC ......... C07D 311/72; B01J 39/05; B01J 39/18; B01J 41/07; B01J 41/12; B01J 47/028; B01J 49/08; B01J 49/50; B01J 49/57; B01J 41/05; B01J 49/07; B01J 47/026; B01D 15/1871; B01D 15/363; B01D 15/424; B01D 15/36; C11C 3/003; C11C 3/08; C11C 3/10; C11C 3/04; C11B 11/00
See application file for complete search history.

(56) References Cited

U.S. PATENT DOCUMENTS

2017/0334875 A1 11/2017 Shibasaki-Kitakawa et al.

FOREIGN PATENT DOCUMENTS

| GB | 1295386 A | * | 11/1972 | ......... B01D 15/1871 |
|----|-----------|---|---------|------------------------|
| JP | H08-059647 A | | 3/1996 | |
| JP | H10-508605 A | | 8/1998 | |
| JP | 2002-194381 A | | 7/2002 | |
| JP | 2005-536191 A | | 12/2005 | |
| JP | 2006-104316 A | | 4/2006 | |
| JP | 2007-014871 A | | 1/2007 | |
| JP | 2007-176801 A | | 7/2007 | |
| JP | 2007-521382 A | | 8/2007 | |
| JP | 2007-297611 A | | 11/2007 | |
| JP | 2009-190989 A | | 8/2009 | |
| JP | 5700188 B2 | | 4/2015 | |
| JP | 2016-059833 A | | 4/2016 | |
| JP | 2016-216456 A | | 12/2016 | |
| WO | 96/014311 A1 | | 5/1996 | |
| WO | 2003/092709 A1 | | 11/2003 | |
| WO | 2005/051294 A2 | | 6/2005 | |

OTHER PUBLICATIONS

Hiromori, K., "Novel simple process for tocopherols selective recovery from vegetable oils by adsorption and desorption with an anion-exchange resin." Food chemistry 194 (2016): 1-5.*
JP,2009190989,A WIPO English Machine Translation; accessed online Mar. 16, 2020.pdf.*
Diaion Product Data Sheet No. 01-04-A-4402 p. 1-2; accessed online Mar. 16, 2020.*
Eitsuka, T. et al., "Down-Regulation of Telomerase Activity in DLD-1 Human Colorectal Adenocarcinoma Cells by Tocotrienol", Biochem and Biophys. Res. Commun., 2006, vol. 348, pp. 170-175.
Shibasaki-Kitakawa, N. et al., "Biodiesel Production Using Anionic Ion-Exchange Resin as Heterogeneous Catalyst", Bioresource Technol., 2007, vol. 98, pp. 416-421.
May 1, 2018 Search Report issued in International Patent Application No. PCT/JP2018/005526.
Aug. 20, 2019 International Preliminary Report on Patentability issued in International Patent Application No. PCT/JP2018/005526.

* cited by examiner

*Primary Examiner* — John M Mauro
(74) *Attorney, Agent, or Firm* — Oliff PLC

(57) ABSTRACT

A vitamin E production method and a vitamin E production device which can highly purify vitamin E in a vitamin E concentrated fraction are provided. A raw oil supply section supplies a raw oil to a series column in which two or more columns including a strongly basic anion exchanger are coupled in series to adsorb vitamin E included in the raw oil on the strongly basic anion exchanger of at least one column from among the series column. A desorption solution supply section supplies a desorption solution to a column on which vitamin E has been adsorbed to desorb vitamin E from the strongly basic anion exchanger of the column.

7 Claims, 1 Drawing Sheet

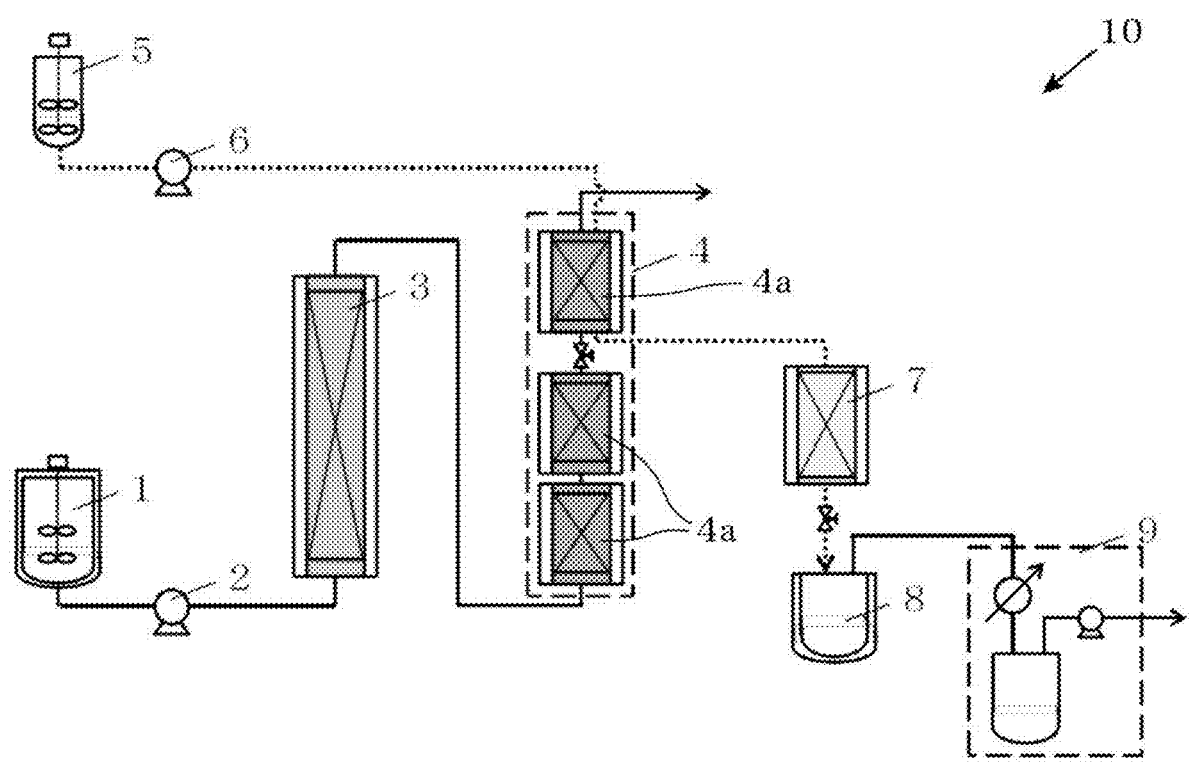

VITAMIN E PRODUCTION METHOD AND VITAMIN E PRODUCTION DEVICE

FIELD OF THE INVENTION

The present invention relates to a vitamin E production method and a vitamin E production device.

DESCRIPTION OF RELATED ART

Vitamin E (tocotrienol and tocopherol) has attracted attention as health functional substances having a high antioxidant activity. In particular, tocotrienol has a basic structure equal to that of tocopherol (common vitamin E) and three double bonds on the side chain, and thus has a nearly 50-fold higher antioxidant activity than tocopherol (see, for example, Non-patent Literature 1). Pharmaceutical activities of tocotrienol, which have not been found in tocopherol, such as arteriosclerosis-improving effects and anticancer effects, have been recently reported (see, for example, Non-patent Literature 2), and it has been expected that tocotrienol will be proactively used in the pharmaceutical and food fields.

However, while tocopherol is widely included in various vegetable oils such as soy, rapeseed, sunflower and corn, tocotrienol is included in some vegetable oils such as palm and rice bran at very low concentration. In addition, tocotrienol easily undergoes oxidative decomposition by heat due to the double bonds on the side chain, and easily loses its activities.

As a raw oil for producing these vitamin E, a deodorizer distillate (scum oil, etc.) discharged in a deodorization step during the production of food oil is used. For every deodorizer distillate, the vitamin E content thereof is tens of times higher than that of raw oils; however, the main component of deodorizer distillate is free fatty acids, and it further includes triglycerides, sterols and various hydrocarbons.

Therefore, no matter either vitamin E is targeted, a step of producing a vitamin E concentrated fraction by separating and recovering a fraction including the vitamin E from a raw material as well as a step of highly purifying vitamin E by separating and removing impurities in the concentrated fraction are required. For the latter separation step for high-purification, various chromatographic separation methods have been proposed, and $\alpha$, $\beta$, $\gamma$, $\delta$-isomers of tocopherol and tocotrienol can be separated as needed. However, due to the large amount of eluent required and the long elution time, there are problems peculiar to chromatographic separation methods, such as issues of increased production costs and burden placed on the environment by waste liquids.

Further, as for the former step of producing a concentrated fraction, a multistage molecular distillation method using the difference between the boiling point of the components is applied, and this method has been already used in the industrial field with regards to tocopherol (see, for example, Patent Literatures 1 to 5). In the conventional step of producing a concentrated fraction, however, due to the greatness in loss by thermal decomposition and the large degree of contamination caused by components having close separation properties, such as free fatty acids and sterols, there has been a problem in that both the recovery rate and purity of tocopherol in a concentrated fraction are about 50 mass %, leading to a cost increase.

Furthermore, when this distillation method is applied to a deodorizer distillate derived from rice bran or palm including tocotrienol, due to the thermal stability of tocotrienol being lower, there has been a problem that the recovery rate and purity are very low, namely several tens of percent by mass.

In order to solve these problems, the present inventors and the like provide a method for producing a vitamin E concentrated fraction by adsorbing vitamin E included in a raw material on a strongly basic anion exchanger under mild conditions of 50° C. under atmospheric pressure, and then desorbing the vitamin E from the ion exchanger (see, for example, Patent Literature 6). Since this method does not need distillation operation at high temperature, it can prevent thermal decomposition of vitamin E such as tocotrienol and can increase the recovery rate and purity of vitamin E. It should be noted that various strongly basic anion exchangers have been developed (see, for example, Patent Literature 7 or 8), any of which can be used in this method.

Furthermore, the present inventors and the like provide, as the high-purification step of the obtained vitamin E concentrated fraction, a method for high-purification of vitamin E by bringing the obtained vitamin E concentrated fraction into contact with a weakly basic anion exchanger to adsorb free fatty acids as impurities on the ion exchanger to remove them from the concentrated fraction (see, for example, Patent Literature 9). In addition, in order to repeatedly use a weakly basic anion exchanger in this method, a regeneration operation to desorb the adsorbed free fatty acids and then provide an adsorption activity again is required. Such a procedure is also developed by the present inventors and the like (see, for example, Patent Literature 10 or 11).

CITATION LIST

Patent Literature

Patent Literature 1: JP-W-10-508605
Patent Literature 2: JP-A-2002-194381
Patent Literature 3: JP-A-2005-536191
Patent Literature 4: JP-A-2007-521382
Patent Literature 5: JP-A-2007-176801
Patent Literature 6: JP-B 1-5700188
Patent Literature 7: JP-A-2006-104316
Patent Literature 8: JP-A-2007-297611
Patent Literature 9: JP-A-2016-216456
Patent Literature 10: JP-A-2007-014871
Patent Literature 11: JP-A-2016-59833

Non-Patent Literature

Non-patent Literature 1: T. Eitsuka, K. Nakagawa, T. Miyazawa, "Down-regulation of telomerase activity in DLD-1 human colorectal adenocarcinoma cells by tocotrienol", Biochem Biophys. Res. Commun., 2006, 348, 170

Non-patent Literature 2: N. Shibasaki-Kitakawa, H. Honda, H. Kuribayashi, T. Toda, T. Fukumura, and T. Yonemoto, "Biodiesel production using anion ion-exchange resin as heterogeneous catalyst", Bioresource Technol., 2007, 98, 416

SUMMARY OF THE INVENTION

However, the vitamin E concentrated fraction produced using the method in Patent Literature 6 still includes relatively many free fatty acids as impurities. Therefore, when highly purifying the vitamin E concentrated fraction using the methods in Patent Literatures 9 to 11, a large amount of solution is required to regenerate a weakly basic anion exchanger, and moreover, it takes time for the regeneration. Accordingly, the production efficiency of vitamin E is reduced.

In addition, the concentration of free fatty acid remaining in a vitamin E concentrated fraction depends on the concentration of vitamin E and the concentration of free fatty acid in the raw oil used in the step of producing a concentrated fraction, and largely varies depending on the origin of the raw materials and the operation of removing free fatty acids as the pretreatment. In particular, when a raw material derived from palm is used, a large amount of free fatty acid remains in the vitamin E concentrated fraction. Therefore, in order to remove this by adsorbing it on a weakly basic anion exchanger, a large amount of exchanger is required, leading to a cost increase. Accordingly, it is unrealistic to use the process industrially.

In order to reduce the cost and prevent decrease in production efficiency in such a high-purification step, it is desired to produce a vitamin E concentrated fraction with the highest possible purity of vitamin E in the preceding step of producing a vitamin E concentrated fraction. Thus, development of a method and a device for further purifying vitamin E in a vitamin E concentrated fraction has been anticipated.

The present invention was made with a focus on such problems, and an object thereof is to provide a vitamin E production method and a vitamin E production device which can highly purify vitamin E in a vitamin E concentrated fraction.

As a result of diligent investigation to achieve the abovementioned object, the present inventors found that, by pushing out the vitamin E from the strongly basic anion exchange resin while concentrating them utilizing the properties of free fatty acids which have a higher acidity than vitamin E and are easily adsorbed on the strongly basic anion exchange resin in comparison to vitamin E, a region of vitamin E adsorbed on a strongly basic anion exchange resin moves within a column thereby realizing the present invention.

That is, the vitamin E production method according to the present invention is a vitamin E production method for recovering vitamin E included in a raw oil, the method being characterized by having an adsorption step of supplying the raw oil to a series column in which two or more columns including a strongly basic anion exchanger are coupled in series, thereby adsorbing vitamin E included in the raw oil on the strongly basic anion exchanger of at least one column from among the series column, and a desorption step of supplying a desorption solution to a column on which vitamin E has been adsorbed in the adsorption step, thereby desorbing the vitamin E from the strongly basic anion exchanger of the column.

The vitamin E production device according to the present invention is a vitamin E production device for recovering vitamin E included in a raw oil, the device being characterized by having a series column in which two or more columns including a strongly basic anion exchanger are coupled in series, a raw oil supply section provided so as to supply the raw oil to the series column, and a desorption solution supply section provided so as to supply a desorption solution which can desorb vitamin E from the strongly basic anion exchanger to at least one column from among the series column, wherein the device is configured so that, when the raw oil is supplied to the series column by the raw oil supply section, vitamin E included in the raw oil is adsorbed on the strongly basic anion exchanger of at least a column to which the desorption solution is supplied by the desorption solution supply section.

The vitamin E production method according to the present invention is suitably carried out by the vitamin E production device according to the present invention. The vitamin E production method and vitamin E production device according to the present invention desorbs and recovers vitamin E from the strongly basic anion exchanger of at least one column, on which vitamin E has been adsorbed, from among a plurality of columns through which the raw oil passes; hence compared to a conventional method for adsorbing and desorbing vitamin E using only one column, the vitamin E in a vitamin E concentrated fraction is highly purified. In particular, the vitamin E in a vitamin E concentrated fraction can be further purified by recovering vitamin E from a column with the highest adsorbed vitamin E amount.

The raw oil of the vitamin E production method and vitamin E production device according to the present invention is not particularly restricted as long as vitamin E such as tocotrienol or tocopherol is included and can be a natural oil (crude oil), a synthetic oil or a mixture thereof. Moreover, the oil can be a modified oil in which part of the abovementioned oils is modified by treatment such as oxidation or reduction, or oil products having the abovementioned oils as a main component. Further, a deodorizer distillate (scum oil) or a fatty acid oil, which are by-products in the purification step for food oil, dark oil and the like, or an unprocessed raw oil (crude oil) can be used. Furthermore, in terms of the quantity of production, when tocotrienol is the target, oils derived from rice bran and palm are preferred, and when tocopherol is the target, oils derived from soy and rapeseed are preferred. In addition, while the raw oil may include free fatty acids, it is desired that free fatty acids be removed as much as possible.

Vitamin E includes α-, β- and δ-tocotrienols, α-, β-, γ- and δ-tocopherols, and the like. In addition, in the specification, high-purity vitamin E indicates vitamin E with a purity wherein the content (mass %) of vitamin E as opposed to the total weight (mass) of vitamin E and remaining components other than vitamin E as impurities minus the solvent is 80 mass % or more, preferably 85 mass % or more, even preferably 90 mass % or more, further desirably 95 mass % or more.

In the vitamin E production method and vitamin E production device according to the present invention, the strongly basic anion exchanger can be an existing one described in, for example, Patent Literatures 7 and 8, and is particularly preferably a strongly basic anion exchange resin. The strongly basic anion exchange resins include, for example, gel, porous and highly porous types when classified by the degree of cross-linking or porosity, and are preferably porous and highly porous types with a large surface area. In addition, commercially available strongly basic anion exchangers can be, for example, DIAION PA-306 (manufactured by Mitsubishi Chemical Corporation), DIAION PA-306S (the same), DIAION PA-308 (the same), DIAION HPA-25 (the same), DOWEX 1-X2 (manufactured by Dow Chemical), Amberlite IRA-45 (manufactured by Organo Corporation), Amberlite IRA-94 (the same), and the like. In addition, the strongly basic anion exchangers can be, for example, DIAION SA20A (manufactured by Mitsubishi Chemical Corporation) and DIAION SA21A (the same) as commercially available products which satisfy pKa 9.8 or less, and DIAION PA408 (the same), DIAION PA412 (the same) and DIAION PA418 (the same) which are porous type II strongly basic anion exchange resin, and the like. Here, type II strongly basic anion exchange resin indicates an anion exchange resin having dimethylethanol ammonium groups.

In order to increase the adsorption efficiency of vitamin E, it is preferred that a raw oil be supplied so that the linear velocity in each column be 0.1 to 4.0 cm/min in the adsorption step of the vitamin E production method according to the present invention. In the vitamin E production device according to the present invention, it is preferred that the raw oil supply section be configured so as to supply a raw oil so that the linear velocity in each column will be 0.1 to 4.0 cm/min.

Further, to increase the desorption efficiency of vitamin E, in the vitamin E production method according to the present invention, it is preferable that the desorption solution is obtained from an acid solution, and the desorption solution is supplied in the desorption step so that the linear velocity in each column will be 0.1 to 4.0 cm/min. In the vitamin E production device according to the present invention, the desorption solution is obtained from an acid solution, and the desorption solution supply section is preferably configured so as to supply the desorption solution so that the linear velocity in each column will be 0.1 to 4.0 cm/min. In this case, as the acid solution, an organic acid such as formic acid, acetic acid or citric acid or a salt thereof, or a mixture thereof can be used. In particular, as the acid solution, a weak acid or weak acid salt solution, such as a mixed solution of acetic acid or citric acid and an alcohol such as ethanol, is suitable.

Within the high-purity vitamin E produced by the vitamin E production method and vitamin E production device according to the present invention, substances other than free fatty acids, such as sterols and squalene, for example, may be included as impurities in an optional amount. Since these substances do not have toxicity, they are not particularly required to be removed except for the purpose of further purifying vitamin E. In addition, in each step, a solvent obtained from alcohols such as ethanol and/or organic acids such as formic acid, acetic acid and citric acid or salts thereof is preferably used.

In addition, among the plurality of columns, the column on which vitamin E is easily adsorbed varies depending on the components of a raw oil; hence, in the desorption step of the vitamin E production method according to the present invention, it is preferred that vitamin E be desorbed from the strongly basic anion exchanger of the column on which vitamin E is easily adsorbed. In the vitamin E production device according to the present invention, the desorption solution supply section is preferably provided so as to supply a desorption solution to a column on which vitamin E is easily adsorbed.

In particular, in the desorption step of the vitamin E production method according to the present invention, vitamin E may be desorbed from the strongly basic anion exchanger of at least one column from among the series column, except for a column through which the raw oil flows first, and the vitamin E may also be desorbed from the strongly basic anion exchanger of, from among the series column, at least a column through which the raw oil flows last. In the vitamin E production device according to the present invention, the desorption solution supply section may be provided so as to supply the desorption solution to at least one column from among the series column, except for a column through which the raw oil flows first, and may also be provided so as to supply the desorption solution to, from among the series column, at least a column through which the raw oil flows last. In these cases, since free fatty acids are more easily adsorbed on a strongly basic anion exchange resin than vitamin E included in a raw oil, vitamin E is not easily adsorbed on the strongly basic anion exchanger of a column through which the raw oil flows first, and vitamin E is more easily adsorbed on the strongly basic anion exchanger of a column through which the raw oil flows last. Therefore, a higher purity vitamin E concentrated fraction can be obtained.

In addition, in these cases, it is preferred that, in the series column, the number of columns coupled in series and the length of each column along a direction through which the raw oil flows be designed depending on the concentration ratio of vitamin E and free fatty acid included in the raw oil supplied to the column. For example, when vitamin E is desorbed from the strongly basic anion exchanger of a column through which a raw oil flows last, the lengths of columns coupled in series are all designed to be the same, and the number of columns can be represented by: number of columns=(concentration of free fatty acid+concentration of vitamin E)/concentration of vitamin E [numbers after the decimal point are rounded or cleared]. Alternatively, the number of columns coupled in series may be designed to be two, and the length ratio of two columns (length of column through which a raw oil flows first/length of column through which a raw oil flows last) and the concentration ratio of free fatty acid and vitamin E (concentration of free fatty acid/concentration of vitamin E) may have the almost same value. As such, by appropriately designing the number of columns coupled in series and the length of columns, vitamin E included in the raw oil can be recovered at high purity, and high-purity vitamin E concentrated fraction can be produced.

The vitamin E production method according to the present invention may have a high-purification step for producing high-purity vitamin E from a vitamin E concentrated fraction including vitamin E desorbed in the desorption step. The vitamin E production device according to the present invention may have a purification column, which is coupled to at least one column among those to which a desorption solution is supplied by the desorption solution supply section, and which produces high-purity vitamin E from a vitamin E concentrated fraction including vitamin E desorbed by the desorption solution. This purification column is preferably filled with a weakly basic anion exchanger. In this case, since free fatty acids desorbed along with vitamin E are adsorbed on the weakly basic anion exchanger and thus removed from the solution, high-purity vitamin E can be more efficiently produced. Any method can be used in the high-purification step and purification column as long as vitamin E can be highly purified, and, for example, methods described in Patent Literatures 9 to 11 can be used. When using the methods described in Patent Literatures 9 to 11, since the purity of vitamin E in a vitamin E concentrated fraction obtained in the step preceding the high-purification step and purification column is high, the weakly basic anion exchanger is more easily regenerated and the number of weakly basic anion exchangers can also be reduced. Therefore, the cost can be reduced, and the production efficiency of vitamin E can also be increased. When the desorption solution is supplied to a plurality of columns, the purification column only needs to be coupled to a column to which the desorption solution is supplied, and it is not necessary to have it coupled to a column to which the desorption solution supply section is coupled.

Because free fatty acids are also adsorbed on a strongly basic anion exchanger, when a raw oil including a large amount of free fatty acids are supplied to the strongly basic anion exchanger, the free fatty acids are also adsorbed on the strongly basic anion exchanger. Therefore, in the step before adsorbing vitamin E included in the raw oil on the strongly basic anion exchanger, it is desired that the free fatty acids be removed as much as possible. As a means thereof, a removing method of saponifying (solidifying) through neutralization, or a method of converting (esterifying) them to non-adsorbable fatty acid esters, or the like, is used. The esterification means can be appropriately selected from known means. Among them, it is preferred that free fatty acids included in the raw oil be esterified by a cation exchanger, particularly a strongly acid cation exchanger.

Therefore, the vitamin E production method according to the present invention preferably has a conversion step of converting a free fatty acid included in the raw oil to a fatty acid ester before the adsorption step. In particular, in the conversion step, it is preferable to convert them to fatty acid ester using a cation exchanger. The vitamin E production device according to the present invention preferably further has a conversion section to fatty acid esters which is arranged between the raw oil supply section and the series column, and is provided to convert a free fatty acid included in the raw oil supplied from the raw oil supply section to a fatty acid ester, supplying it to the series column thereafter. In particular, the conversion section to fatty acid esters preferably has a cation exchanger which can convert the free fatty acid to the fatty acid ester.

As the cation exchanger, for example, known cation resins such as DIAION PK series (manufactured by Mitsubishi Chemical Corporation), DIAION SK series (the same), DOWEX 50W series (manufactured by Dow Chemical), Amberlyst series (manufactured by Organo Corporation), Amberlite series (the same), Amberjet series (the same), MonoPlus S108 (manufactured by LANXESS), MonoPlus S108H (the same), MonoPlus S112 (the same), CNP 80WS (the same), and S1668 (the same) can be used.

The free fatty acids included in the raw oil are, for example, organic acids having 1 to 30 carbon number, or those including at least one of organic acids having 1 to 30 carbon number. Typical examples thereof are oleic acid, linoleic acid, linolenic acid, palmitic acid, stearic acid, and the like.

The vitamin E production method according to the present invention may have a stopping step of measuring the concentration of vitamin E included in the discharge solution flowing out from the series column during the adsorption step, and stopping the supply of the raw oil to the series column before the concentration reaches the concentration of vitamin E included in the raw oil. In this case, the supply of the raw oil is preferably stopped after vitamin E is detected, and more preferably stopped before the concentration reaches half the concentration of vitamin E in the raw oil.

In this case, examples of the method (means) for measuring the concentration of vitamin E in the raw oil or in the discharge solution flowing out from the series column include, for example, means using high performance liquid chromatograph equipped with a fluorescence detector, a UV detector, an evaporative light scattering detector or a mass spectrometer, gas chromatograph equipped with a flame ionization detector or a mass spectrometer, or a thin-layer chromatograph. In addition, to estimate the amount of vitamin E adsorbed on each column, it is preferred that the concentration of vitamin E in each solution flowing out from the outlet of each column be measured online.

The vitamin E production method according to the present invention may have a measurement step of measuring the concentration of vitamin E included in the discharge solution flowing out from the series column during the adsorption step, and in the desorption step, the vitamin E may be desorbed from the strongly basic anion exchanger of a column selected based on the measured result in the measurement step. In this case, the concentration of vitamin E in the discharge solution from the series column can be measured to grasp the movement state thereof, thereby determining the column in which a vitamin E adsorption region exists. Therefore, a column in which a high-purity vitamin E adsorption region exists can be selected based on a measured result in the measurement step, and high-purity vitamin E can be produced. In addition, in the desorption step, a column including the high-purity vitamin E adsorption region can be selectively released, for example, by switching between the lines using a switching means for solution flows, to desorb vitamin E.

According to the present invention, it is possible to provide a vitamin E production method and a vitamin E production device, which can highly purify vitamin E in a vitamin E concentrated fraction.

BRIEF DESCRIPTION OF THE DRAWINGS

FIG. 1 is a configuration diagram which shows a vitamin E production device of an embodiment of the present invention.

DETAILED DESCRIPTION OF THE INVENTION

The embodiment of the present invention will now be described based on the drawing and examples.

FIG. 1 shows the vitamin E production method and vitamin E production device of an embodiment of the present invention.

As shown in the FIGURE, the vitamin E production device 10 has a raw oil supply section 1, a raw oil supply pump 2, a conversion section to fatty acid esters 3, a series column 4, a desorption solution supply section 5, a desorption solution pump 6, a purification column 7, a vitamin E recovery section 8, and a solvent removal section 9.

The raw oil supply section 1 stores a raw oil as the raw material. The raw oil supply pump 2 is provided between the raw oil supply section 1 and the conversion section to fatty acid esters 3 so as to supply the raw oil stored in the raw oil supply section 1 to the conversion section to fatty acid esters 3. The conversion section to fatty acid esters 3 has a cation exchanger which can convert a free fatty acid to a fatty acid ester. The conversion section to fatty acid esters 3 is provided to convert a free fatty acid included in the raw oil supplied from the raw oil supply section 1 to a fatty acid ester by a cation exchanger, which fatty acid ester is then supplied to the series column 4.

The series column 4 has two or more columns 4a including a strongly basic anion exchanger, and is configured by coupling the columns 4a in series. The series column 4 is configured to allow a discharge solution from the conversion section to fatty acid esters 3 to flow through columns 4a sequentially. Therefore, in the series column 4, vitamin E included in the raw oil is adsorbed on the strongly basic anion exchanger of at least one column 4a.

The desorption solution supply section 5 stores a desorption solution which can desorb vitamin E from the strongly basic anion exchanger. The desorption solution pump 6 is provided between the desorption solution supply section 5 and series column 4. The desorption solution pump 6 can supply the desorption solution stored in the desorption solution supply section 5 to at least one column 4a, on which vitamin E has been adsorbed, from among the series column 4. The purification column 7 is coupled to at least one column 4a to which the desorption solution is supplied by the desorption solution supply section 5. The purification column 7 is filled with a weakly basic anion exchanger and is configured to produce high-purity vitamin E from a vitamin E concentrated fraction including the vitamin E desorbed by the desorption solution.

In a specific example shown in the FIGURE, the series column 4 has 3 columns 4a. The desorption solution is supplied via the desorption solution pump 6 from the desorption solution supply section 5 to, from among the series column 4, a column 4a through which a raw oil flows last. In addition, the purification column 7 is coupled to a column 4a through which the raw oil flows last.

The vitamin E recovery section 8 is connected to the purification column 7 and can recover high-purity vitamin E produced in the purification column 7. The solvent removal section 9 is connected to the vitamin E recovery section 8, and removes the solvent used in each step from the vitamin E recovered in the vitamin E recovery section 8 as needed.

The vitamin E production device 10 can suitably carry out the vitamin E production method in the embodiment of the present invention. That is, in the vitamin E production method in the embodiment of the present invention, first, a raw oil included in the raw oil supply section 1 is supplied to the conversion section to fatty acid esters 3 by the raw oil supply pump 2, and free fatty acids included in the raw oil are converted to fatty acid esters in the conversion step. Then, in the adsorption step, a discharge solution flowing out from the conversion section to fatty acid esters 3 is supplied to the series column 4, and vitamin E and unreacted free fatty acids included in the discharge solution are adsorbed competitively on the strongly basic anion exchanger of each column 4a in the series column 4.

After that, in the desorption step, a desorption solution is supplied from the desorption solution supply section 5 via the desorption solution pump 6 to a column 4a, on which vitamin E has been adsorbed, from among the series column 4 in order to desorb vitamin E. Therefore, a high-purity vitamin E concentrated fraction can be produced. Furthermore, in the high-purification step, vitamin E desorbed from the series column 4 is supplied to the purification column 7, and vitamin E with even higher purity can be produced. The obtained vitamin E is recovered in the vitamin E recovery section 8, and solvents can also be removed in the solvent removal section 9 as needed.

The vitamin E production method and vitamin E production device 10 in the embodiment of the present invention desorbs and recovers vitamin E from the strongly basic anion exchanger of at least one column 4a, on which vitamin E has been adsorbed, from among a plurality of columns 4a through which a raw oil has passed; hence, compared to a conventional one for adsorbing and desorbing vitamin E using only one column, it can highly purify vitamin E in a vitamin E concentrated fraction. In particular, by recovering vitamin E from a column 4a having the highest amount of adsorbed vitamin E, the purity of vitamin E in the vitamin E concentrated fraction can be further enhanced.

The vitamin E production method and vitamin E production device 10 in the embodiment of the present invention can produce vitamin E of higher purity because, in the purification column 7, free fatty acids desorbed with vitamin E are adsorbed on the weakly basic anion exchanger and removed from the vitamin E concentrated fraction after desorption. In addition, because the purity of vitamin E in the vitamin E concentrated fraction after desorption is high, the weakly basic anion exchanger can be easily regenerated and the number of weakly basic anion exchangers can also be reduced. Therefore, the cost can be reduced, and the production efficiency of vitamin E can also be increased.

In addition, the vitamin E production device 10 can be simply and successively operated to produce high-purity vitamin E, and high-purity vitamin E can be inexpensively produced on a large scale. The vitamin E production method and vitamin E production device 10 in the embodiment of the present invention can produce high-purity vitamin E with a vitamin E purity of 95 mass % or more from, for example, a raw oil with a vitamin E content of about 0.5 to 20 mass %, in particular a raw oil such as a deodorizer distillate including free fatty acids as a main component as well as triglycerides, sterols and the like as the other components.

EXAMPLE

The present invention will now be described in detail in accordance with examples. It should be noted, however, that the technical scope of the present invention is not restricted in any way by the description. Unless otherwise specified, the following examples were carried out in accordance with common methods known to people skilled in the art.

Experiment for Producing High-Purity Vitamin E Using Multiple Columns

Experimental Method and Procedure

Commercially available δ-tocopherol (pKa 12.6) was used as vitamin E, and oleic acid (pKa 4.8), included the most in a vegetable oil, was used as the free fatty acid. As a solvent used in each step, ethanol was used. It should be noted that ethanol is also a reactant of the esterification reaction in the conversion section to fatty acid esters 3. In addition, as the strongly basic ion exchanger, used was the exchanger obtained by replacing, by a known means, the functional group of a porous and strongly basic anion exchange resin "DIAION PA306S (manufactured by Mitsubishi Chemical Corporation)" with an OH-type functional group having an adsorption activity. As for the series column 4, the total amount of strongly basic anion exchange resin to be filled in was set at 20 g (wet weight), the internal diameter was set at 1.1 cm and the fixed total column length was set at 30 cm, and such a column was equally divided into a plurality of columns 4a along the length direction, and the series column obtained by coupling said columns 4a in series was used.

The experimental conditions are shown in Table 1. In Example 1, with raw material derived from rice bran in mind, a solution in which the concentration of free fatty acid and the concentration of vitamin E are equal was used as the raw material. As for the series column 4, a 30 cm column was divided into two in the length of 15 cm each, and the series column obtained by coupling the resulting column A and column B in series was used (column A and column B in the order from the top). Both the column A and the column B have a column length (column height) of 15 cm. Meanwhile, in Example 2, with raw material derived from palm in mind, a solution in which the concentration of free fatty acid is two-times higher than the concentration of vitamin E was used as the raw material. As the series column 4, a 30 cm column was divided into three in the length of 10 cm each, and the series column obtained by coupling the resulting column A, column B and column C in series was used (column A, column B and column C in the order from the top). The column A, the column B and the column C all have a column length (column height) of 10 cm.

TABLE 1

Component concentration in raw material and conditions for dividing columns

| Experimental conditions | Example 1 | Example 2 |
|---|---|---|
| Free fatty acid concentration in raw material [mol/dm$^3$] | 0.05 | 0.10 |
| Vitamin E concentration in raw material [mol/dm$^3$] | 0.05 | 0.05 |
| Divided column height [cm] | 15 | 10 |
| Number of divided columns | 2 | 3 |

In the adsorption step of adsorbing vitamin E, an ethanol mixed solution of vitamin E and free fatty acid (oleic acid) adjusted to a predetermined concentration was supplied as a raw material from the bottom of the series column 4 by an upward flow to column B and column A in this order (Example 1), or to column C, column B and column A in this order (Example 2), to adsorb vitamin E on the series column 4. In the desorption step of desorbing vitamin E, the supply of the raw material was stopped before the concentration of vitamin E included in the discharge solution which had flown out from the column A reached the concentration of vitamin E in the raw material. Thereafter, the column on which vitamin E had been adsorbed (column A in both Examples 1 and 2) was removed from the series column 4, and by supplying ethanol to this column, the raw material remaining in the column was pushed out. Thereafter, an acetic acid-ethanol solution of 0.43 mol/dm$^3$ was supplied as a desorption solution to desorb vitamin E.

For comparison, the same operation was carried out using other columns to desorb adsorbed components. All steps were carried out at 50° C. under atmospheric pressure, and the supply flow rates of the raw material and the desorption solution all were 1.0 cm$^3$/min.

[Results]

In Table 2, the amounts of components recovered from column A on which vitamin E has been adsorbed as well as from other column B and column C, along with the purity of vitamin E based on mass calculated from said amounts both in Example 1 and Example 2 are shown. As shown in Table 2, in both Example 1 and Example 2, it is found that, among the total amount of vitamin E recovered from all columns, 95 mass % or more thereof is recovered from the column A. In addition, the purity of vitamin E recovered from the column A was 96 mass % or more. If recovery is carried out without dividing the series column 4 based on a known procedure, vitamin E is recovered as the total amount (A+B or A+B+C). The purity of vitamin E in this case is about 54 mass % in Example 1 and about 28 mass % in Example 2, and thus, it is found that the purity is significantly improved by dividing the column.

TABLE 2

Amount of components recovered from each column and purity of vitamin E based on weight

| Example 1 | | | |
|---|---|---|---|
| | Column (A + B) | | |
| | A | B | A + B |
| Free fatty acid [mmol] | 0.49 | 9.87 | 10.4 |
| Vitamin E [mmol] | 8.13 | — | 8.13 |
| Purity of vitamin E [mass %] | 96.2 | 0 | 54.4 |

| Example 2 | | | |
|---|---|---|---|
| | Column (A + B + C) | | |
| | A | B + C | A + B + C |
| Free fatty acid [mmol] | 0.079 | 12.0 | 12.1 |
| Vitamin E [mmol] | 3.12 | 0.17 | 3.29 |
| Purity of vitamin E [mass %] | 98.4 | 2.16 | 28.2 |

The above results revealed that high-purity vitamin E of 95 mass % or more can be produced by the vitamin E production method and vitamin E production device 10 in the embodiment of the present invention. As described above, in a common separation method by thin-layer chromatography, separation is carried out using the difference in Rf values between separated components; however, in the vitamin E production method and vitamin E production device 10 in the embodiment of the present invention, the components can be separated depending not only on the difference in ion exchange capacity and adsorptive capacity of the strongly basic anion exchanger between vitamin E and components competitive with vitamin E, but also on the concentration and properties (acidity) of components competitive with vitamin E.

INDUSTRIAL APPLICABILITY

The present invention has, for example, industrial applicability described below:
(1) Vitamin E such as tocotrienol can be produced in good yield at high purity by a simple process, and can be more inexpensively and stably supplied to society, and
(2) By dividing the series column into multistep columns depending on the concentration of vitamin E in a raw material, a low concentration raw material, which were unable to be used in conventional methods, can be used, and an increased amount of vitamin E derived from natural products can be supplied to society.

REFERENCE SIGNS LIST

1: Raw oil supply section
2: Raw oil supply pump
3: Conversion section to fatty acid esters
4: Series column
  4a: Column
5: Desorption solution supply section
6: Desorption solution pump
7: Purification column
8: Vitamin E recovery section
9: Solvent removal section
10: Vitamin E production device

What is claimed is:
1. A vitamin E production method for recovering vitamin E included in a raw oil, the method comprising:
  an adsorption step of supplying the raw oil to a series column in which two or more columns comprising a strongly basic anion exchanger are coupled in series, thereby adsorbing vitamin E included in the raw oil on the strongly basic anion exchanger of at least one column from among the series column, and a desorption step of supplying a desorption solution to a column on which vitamin E has been adsorbed in the adsorption step, except to a column through which the raw oil flows first, thereby desorbing the vitamin E from the strongly basic anion exchanger of the column, wherein the vitamin E is desorbed from the strongly basic anion exchanger of at least one column from among the series column, except for the column through which the raw oil flows first, wherein in the series column, the lengths of columns along a direction through which the raw oil flows are the same, and the number of columns is represented as below using the concentrations of free fatty acid and vitamin E included in the raw oil:

Number of columns=(concentration of free fatty acid+concentration of vitamin $E$)/concentration of vitamin $E$

[numbers after the decimal point are rounded or discarded], and in the desorption step, the vitamin E is desorbed from the strongly basic anion exchanger of, from among the series column, a column through which the raw oil flows last.

2. The vitamin E production method according to claim 1, the method having a conversion step of converting a free fatty acid included in the raw oil to a fatty acid ester before the adsorption step.

3. The vitamin E production method according to claim 2, wherein the conversion step carries out the conversion to the fatty acid ester using a cation exchanger.

4. A vitamin E production method for recovering vitamin E included in a raw oil, the method comprising:

an adsorption step of supplying the raw oil to a series column in which two or more columns comprising a strongly basic anion exchanger are coupled in series, thereby adsorbing vitamin E included in the raw oil on the strongly basic anion exchanger of at least one column from among the series column, and a desorption step of supplying a desorption solution to a column on which vitamin E has been adsorbed in the adsorption step, except to a column through which the raw oil flows first, thereby desorbing the vitamin E from the strongly basic anion exchanger of the column, wherein the vitamin E is desorbed from the strongly basic anion exchanger of at least one column from among the series column, except for the column through which the raw oil flows first, the method having a stopping step of measuring a concentration of vitamin E included in a discharge solution flowing out from the series column during the adsorption step and stopping the supply of the raw oil to the series column before the concentration reaches a concentration of vitamin E included in the raw oil.

5. A vitamin E production device for recovering vitamin E included in a raw oil, the device having a series column in which two or more columns comprising a strongly basic anion exchanger are coupled in series, a raw oil supply section provided so as to supply the raw oil to the series column, and a desorption solution supply section, provided so as to supply to at least one column from among the series column, except for a column through which the raw oil flows first, a desorption solution which can desorb vitamin E from the strongly basic anion exchanger, wherein the device is configured so that, when the raw oil supply section supplies the raw oil to the series column, vitamin E included in the raw oil is adsorbed on the strongly basic anion exchanger of at least a column to which the desorption solution is supplied by the desorption solution supply section, wherein in the series column, the lengths of columns along a direction through which the raw oil flows are the same, and the number of columns is represented as below using the concentrations of free fatty acid and vitamin E included in the raw oil:

Number of columns=(concentration of free fatty acid+concentration of vitamin $E$)/concentration of vitamin $E$

[numbers after the decimal point are rounded or discarded], and wherein the desorption solution supply section is provided so as to supply the desorption solution to, from among the series column, a column through which the raw oil flows last.

6. The vitamin E production device according to claim 5, further having a conversion section to fatty acid esters which is arranged between the raw oil supply section and the series column and is provided to convert a free fatty acid included in the raw oil supplied from the raw oil supply section to a fatty acid ester, which is then supplied to the series column.

7. The vitamin E production device according to claim 6, wherein the conversion section to fatty acid esters has a cation exchanger, which can convert the free fatty acid to the fatty acid ester.

* * * * *